United States Patent
Ohtsuka

(10) Patent No.: US 8,106,368 B2
(45) Date of Patent: Jan. 31, 2012

(54) FLUORESCENCE DETECTING METHOD

(75) Inventor: Hisashi Ohtsuka, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 331 days.

(21) Appl. No.: 12/465,401

(22) Filed: May 13, 2009

(65) Prior Publication Data
US 2009/0283700 A1    Nov. 19, 2009

(30) Foreign Application Priority Data

May 14, 2008   (JP) .................................. 2008-126685

(51) Int. Cl.
*G01J 1/58*   (2006.01)
(52) U.S. Cl. .................................. 250/459.1; 250/458.1
(58) Field of Classification Search ............... 250/458.1, 250/459.1
See application file for complete search history.

(56) References Cited

FOREIGN PATENT DOCUMENTS
JP    2008-102117 A    5/2008

OTHER PUBLICATIONS

Margarida M. L. M. Vareiro et al., "Surface Plasmon Fluorescence Measurements of Human Chorionic Gonadotrophin: Role of Antibody Orientation in Obtaining Enhanced Sensitivity and Limit of Detection", Analytical Chemistry, Apr. 15, 2005, pp. 2426-2431, vol. 77, No. 8.
Yasushi Inouye et al., "Near field Raman spectroscopy and imaging using a tip enhanced field", Spectral Researches, 2002, pp. 276-285, vol. 51, No. 6.

*Primary Examiner* — Mark R Gaworecki
(74) *Attorney, Agent, or Firm* — Sughrue Mion, PLLC

(57) ABSTRACT

A fluorescence detecting method utilizes surface plasmon enhancement. An electric field enhancing field is caused to be generated at a detecting portion that includes a metal film provided on a surface of a dielectric prism. Fluorescence emitted by fluorescent labels, which are attached to a detection target substance, due to the excitation effect of the electric field enhancing field is detected by a photodetector. During the detection, a plurality of fine metal particles are dispersed on the detecting portion.

14 Claims, 7 Drawing Sheets

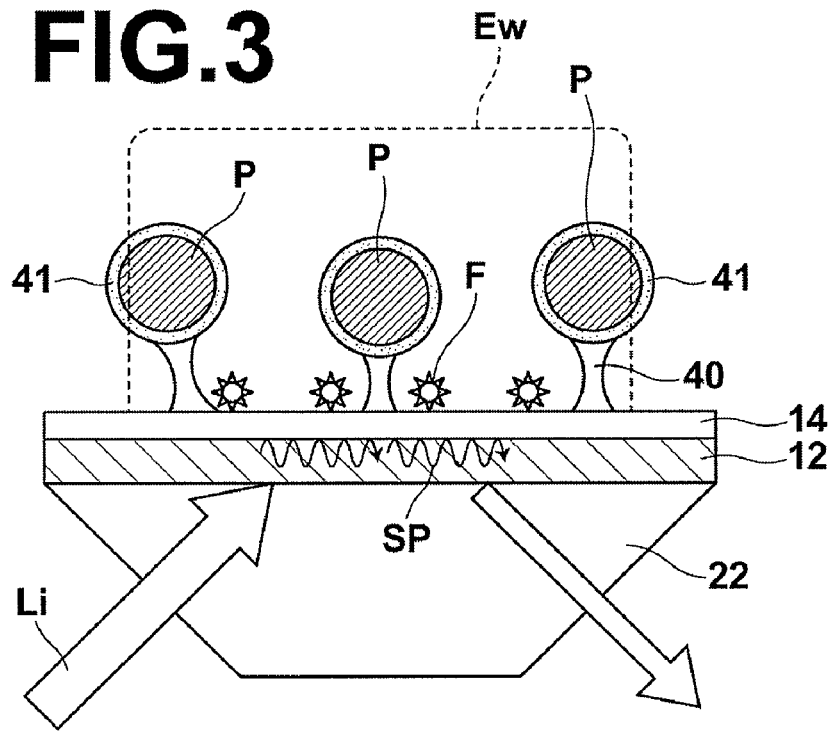
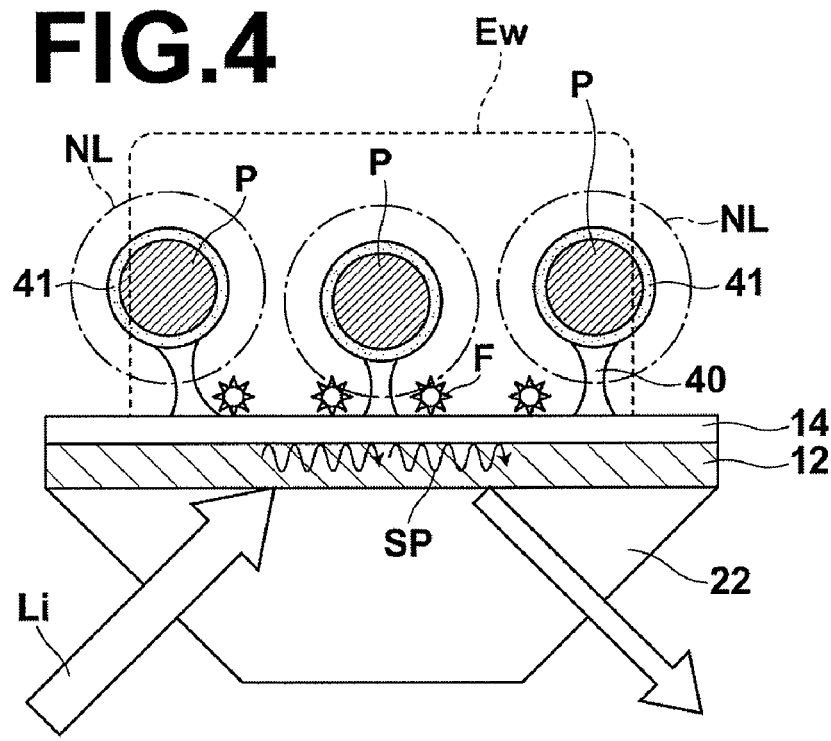

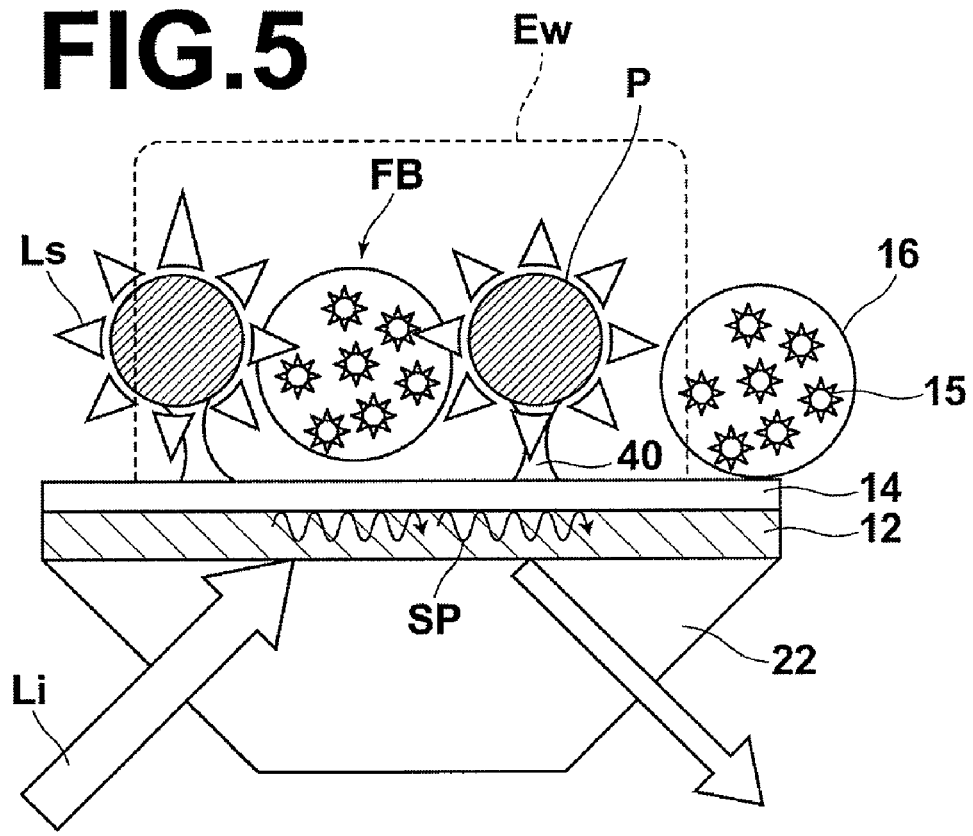

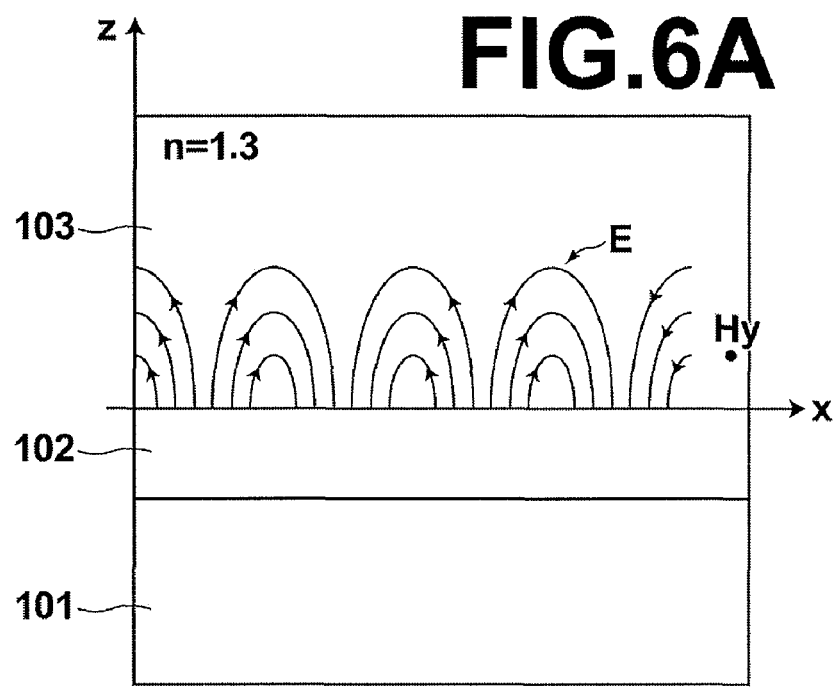
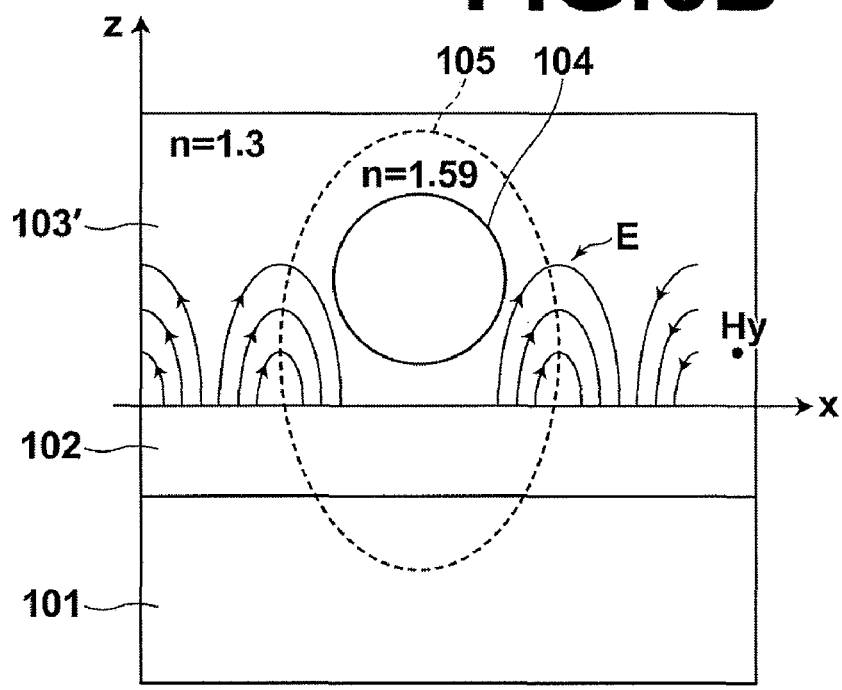

FLUORESCENCE DETECTING METHOD

BACKGROUND OF THE INVENTION

1. Field of the Invention

The present invention is related to a fluorescence detecting method. More particularly, the present invention is related to a fluorescence detecting method that utilizes surface plasmon.

2. Description of the Related Art

Fluorometry is conventionally used in for biological measurements and the like, as an easy and highly sensitive measuring method. In fluorometry, a sample, which is considered to contain a detection target substance that emits fluorescence when excited by light having a specific wavelength, is irradiated with an excitation light beam of the aforementioned specific wavelength. The presence of the detection target substance can be confirmed by detecting the fluorescence due to the excitation. In the case that the detection target substance is not a fluorescent substance, a substance labeled by a fluorescent substance that specifically bonds with the detection target substance is caused to contact the sample. Thereafter, fluorescence is detected in the same manner as described above, thereby confirming the presence of the bond, that is, the detection target substance.

With recent advances in the performance of photodetectors, such as cooled CCD's, fluorometry has become indispensable in biological research. In addition, fluorescent pigments having fluorescence quantum yields that exceed 0.2, which is the standard for practical use, such as FITC (fluorescence: 525 nm, fluorescence quantum yield: 0.6) and Cy5 (fluorescence: 680 nm, fluorescence quantum yield: 0.3) have been developed as fluorescent labeling materials and are being widely used.

Further, high sensitivity detection on the order of 1 pM and less is being realized, by amplifying fluorescence signals employing electric field enhancing fields due to surface plasmon, as described in Japanese Patent Application No. 2006-255374 and by M. M. L. M. Vareiro et al., "Surface Plasmon Fluorescence Measurements of Human Chorionic Gonadotrophin: Role of Antibody Orientation in Obtaining Enhanced Sensitivity and Limit of Detection", Analytical Chemistry, Vol. 77, No. 8, pp. 2426-2431, 2005. This method is referred to as surface plasmon electric field enhanced fluorescent spectroscopy.

Raman spectroscopy using a metal probe which is capable of detecting a substance at the molecular level, as described in Y. Inouye and S. Kawata, "Near field Raman spectroscopy and imaging using a tip enhanced field", Spectral Researches, Vol. 51, No. 6, pp. 276-285, 2002. In this Raman spectroscopy method, light is caused to enter the leading end of a metal probe, to cause local plasmon to be generated. A localized strong electric field which is generated by the local plasmon between the probe and a substrate is utilized. Thereby, the scattering cross sectional area during the Raman process by molecules directly beneath the probe is effectively increased. Theoretically, it is considered that an increased intensity from ten times to 106 times the intensity of incident light can be obtained (refer to section 2.2.1 at page 277 of Y. Inouye and S. Kawata, "Near field Raman spectroscopy and imaging using a tip enhanced field", Spectral Researches, Vol. 51, No. 6, 2002).

However, Raman signals are greatly influenced by the environment and conditions in which detection target substances are placed, such as solvents. In addition, vibrations of foreign substances are also reflected in spectra. Therefore, although Raman spectroscopy is effective for qualitative analysis, expectations cannot be held regarding the quantitative properties thereof. Further, Raman spectroscopy apparatuses are generally large, expensive, and have poor operability.

SUMMARY OF THE INVENTION

The present invention has been developed in view of the foregoing circumstances. It is an object of the present invention to provide a fluorescence detecting method that enables high sensitivity detection on the order of the molecular level over wide detection range, more simply and at lower cost than Raman spectroscopy.

A first fluorescence detecting method of the present invention includes the steps of:

supplying a sample that includes a detection target substance labeled with fluorescent labels F to a detecting portion that includes a metal film formed on a surface of a dielectric prism;

causing an excitation light beam of a wavelength that causes the fluorescent labels F to emit light to enter the interface between the dielectric prism substrate and the metal film through the dielectric prism substrate such that an electric field enhancing field is generated on the surface of the metal film; and detecting fluorescence emitted by fluorescent labels, which are attached to the detection target substance, generated due to an excitation effect of the electric field enhancing field, with a photodetector to detect the amount of the detection target substance which is present in the sample; and is characterized by the detection of the fluorescence being performed with a plurality of fine metallic particles dispersed on the detecting portion.

In the present specification, the "detecting portion" is the location where the sample and the like are supplied, and includes the metal film which is provided on the surface of the dielectric prism. The detecting portion is provided such that when the excitation light beam enters the interface between the dielectric prism substrate and the metal film through the dielectric prism substrate such that conditions for total internal reflection are satisfied, evanescent waves are caused to be generated at the interface and causes surface plasmon to be generated within the metal film by resonance with the evanescent waves.

The term "electric field enhancing field" refers to a local region on the upper surface of the metal film that exhibits an enhancing effect of electric fields, generated due to the evanescent waves which are generated by irradiating the excitation light beam onto the interface between the dielectric plate and the metal film such that conditions for total reflection are satisfied at the interface, and due to surface plasmon which are induced by the evanescent waves and generated within the metal film.

The term "amount of the detection target substance" refers also to whether the detection target substance is present in the sample. That is, the term refers both to a quantitative amount and a qualitative amount.

Hot spots are local regions at which static electric forces become concentrated at fine structures, and as a result, form locally strong electric fields.

Particularly at hot spots which are formed in gaps among fine metallic particles or in gaps among fine metallic particles and the metal film, the electric field which is enhanced by the aforementioned plasmon is concentrated, to form great electric fields. At the same time, a synergistic effect that the great electric fields induce plasmon in the fine metallic particles or in the metal film even further is generated. Therefore, an electric field enhancing field having a far greater intensity will be generated compared to cases in which a single particle is present, or cases in which non metallic particles are in close proximity to each other. For example, in the case that two fine metallic particles are several nm away from each other, the hot spot which is generated in the gap therebetween will be 106 or greater, as described in Y. Inouye and S. Kawata, "Near field Raman spectroscopy and imaging using a tip enhanced field", Spectral Researches, Vol. 51, No. 6, pp. 276-285, 2002.

In the fluorescence detecting method of the present invention, it is preferable for the particle sizes of the fine metallic particles to be within a range from 40 nm to 200 nm. It is also preferable for the fine metallic particles to be nano rods. In addition, it is preferable for the fluorescent labels to be constituted by an anti quenching fluorescent material.

It is preferable for a non flexible film of a hydrophobic material to be formed at a film thickness within a range of 10 to 100 nm on the surface of the metal film opposite the dielectric prism. In this case, it is preferable for the non flexible film to be formed by a polymer material.

In the fluorescence detecting method of the present invention, the fluorescence may be detected by the photodetector after the solvent in the sample is dried.

Here, the term "particle size" of the fine metallic particles refers to the greatest dimension of the fine particles.

Further, "nano rods" are nano fine particles in the shape of rods. The ratios of the longitudinal axes and the horizontal axes thereof (aspect ratios) are generally within a range from 1 to 20.

The "anti quenching fluorescent material" is that in which fluorescent pigment molecules are enveloped in an anti quenching material that transmits fluorescence generated by the fluorescent pigment molecules and prevents metallic quenching. A single fluorescent pigment molecules may be enveloped in the anti quenching material, but it is preferable for a plurality of fluorescent pigment molecules to be enveloped in the anti quenching material. Note that in the case that the anti quenching fluorescent material includes a plurality of fluorescent pigment molecules, a portion of the fluorescent pigment molecules may be exposed to the exterior of the anti quenching material, as long as at least one fluorescent pigment molecule is enveloped therein. Note that metallic quenching is a non radiant form of energy deactivation that occurs in the case that metal is present in the vicinity of fluorescent substances which have absorbed energy and have become excited. The excitation energy is transferred from the fluorescent substances to the metal, and the energy is lost within the metal.

Here, the term "non flexible" refers to a degree of rigidity that does not result in deformation such that the film thickness of the non flexible film changes during normal use of a fluorescence sensor.

The fluorescence detecting method of the present invention detects fluorescence with the plurality of fine metallic particles dispersed on the detecting portion. Thereby, the hot spots which are generated in the gaps among the fine metal particles or the gaps among the fine metal particles and the metal film can enhance the fluorescence generated by the fluorescent labels which are present within the hot spots. The plurality of fine metal particles are widely dispersed on the detecting portion. Therefore, the hot spots are formed over a wide range. As a result, a fluorescence detecting method which is more simple and realized as a lower cost than Raman spectroscopy enables high sensitivity detection on the order of the molecular level. Further, measurements can be performed within short periods of time over a wider range compared to Raman spectroscopy, in which a region that exhibits electric field enhancing effects is limited to the vicinity of the tip of a metallic probe.

In addition, fine metallic particles have greater scattering power with respect to light compared to other fine particles having similar volumes. Therefore, the scattered light can be employed as secondary excitation light, to more efficiently cause the fluorescent pigments to emit light.

BRIEF DESCRIPTION OF THE DRAWINGS

FIG. 3 is a schematic sectional diagram that illustrates the vicinity of a detecting portion, on which fine metallic particles are dispersed, in a fluorescence detecting apparatus that executes a fluorescence detecting method according to the second embodiment of the present invention.

FIG. 4 is a schematic sectional diagram that illustrates the vicinity of a detecting portion, on which fine metallic particles are dispersed, in a fluorescence detecting apparatus that executes a fluorescence detecting method according to a second embodiment of the present invention.

FIG. 5 is a schematic sectional diagram that illustrates the vicinity of a detecting portion, on which fine metallic particles are dispersed, in a fluorescence detecting apparatus that executes a fluorescence detecting method according to a third embodiment of the present invention.

FIG. 6A is a diagram that schematically illustrates electric fields E which are generated in the case that only a water solvent layer is present on a metal film.

FIG. 6B is a diagram that schematically illustrates electric fields E which are generated in the case that an anti quenching substance is present on a metal film.

BEST MODE FOR CARRYING OUT THE INVENTION

Hereinafter, an embodiment of the present invention will be described with reference to the attached drawings. However, the present invention is not limited to the embodiment to be described below.

First Embodiment

Figure 1:
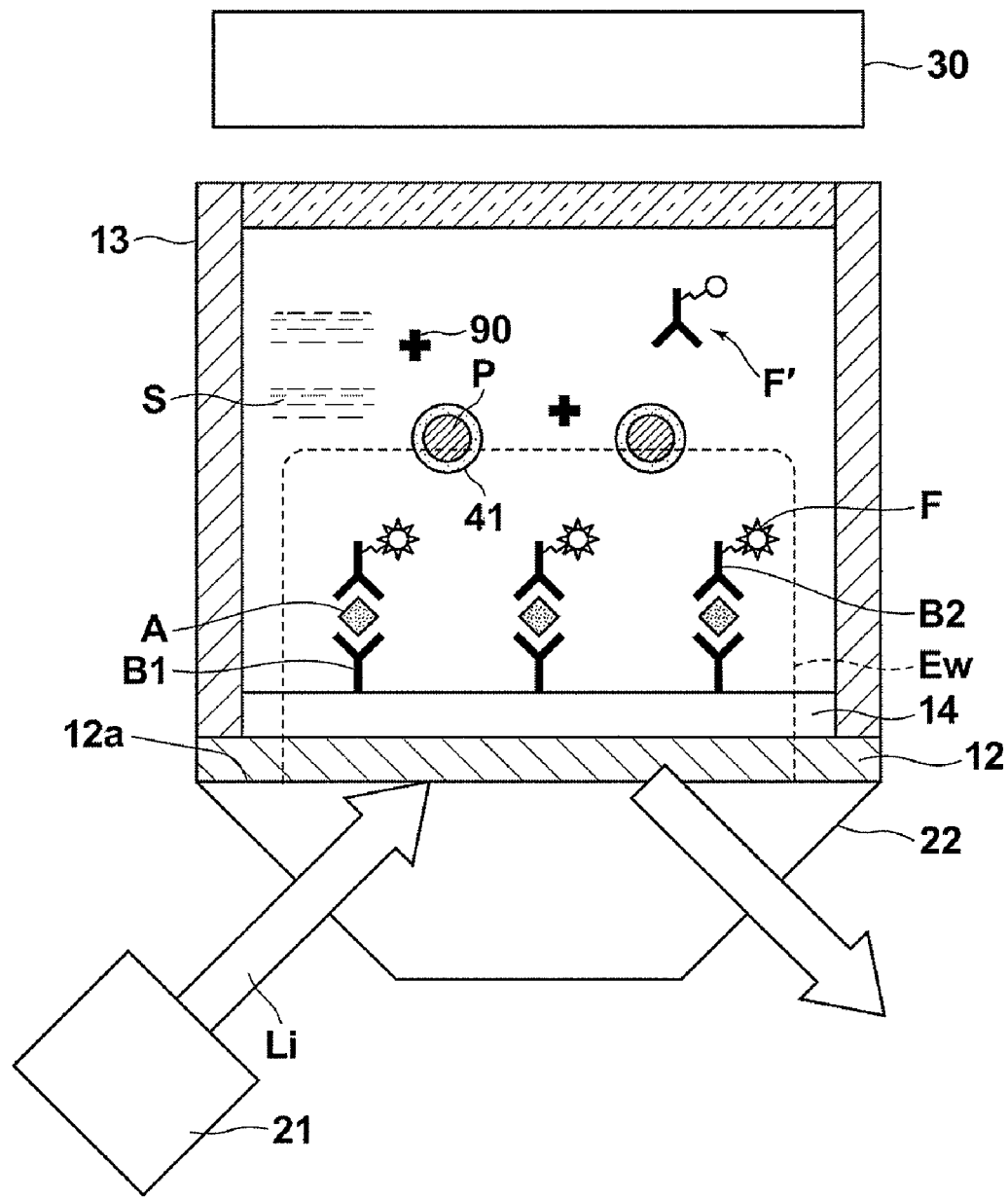
FIG. 1 is a schematic sectional diagram that illustrates a fluorescence detecting apparatus that executes a fluorescence detecting method of the present invention.

FIG. 1 is a schematic sectional diagram that illustrates a fluorescence detecting apparatus that executes the fluorescence detecting method of the present invention. In the first embodiment, a case will be described in which an antigen A is detected as a detection target substance from a sample S that contains the antigen A.

As illustrated in FIG. 1, the fluorescence sensor is equipped with: a light source 21 that emits an excitation light beam Li of a predetermined wavelength; a dielectric prism substrate 22 formed by a material that transmits the excitation light beam Li, provided to cause the excitation light beam Li to propagate therethrough from a first side thereof; a metal film 12, provided on a second side of the dielectric prism substrate 22; a non flexible film 14 which is formed on the metal film 12; primary antibodies which are immobilized onto the non flexible film 14 and that specifically bind with the antigens A; a sample holding section 13 that holds the sample S such that the sample S contacts the non flexible film 14; and a photodetector 30 which is provided at a position at which fluorescence emitted by fluorescent labels F can be detected. FIG. 1 also illustrates fine metallic particles P; the fluorescent labels F included in the sample S; and secondary antibodies B2 provided on the fluorescent labels F. The secondary antibodies B2 also specifically bind with the antigens A.

The excitation light beam Li is not particularly limited as long as it is capable of exciting the fluorescent labels F into emitting fluorescence, and may be a single wavelength light beam emitted from a laser light source or the like, or a broad spectrum light beam emitted from a white light source. The type of light beam to be employed as the excitation light beam Li may be appropriately selected according to detection conditions.

The light source 21 is not particularly limited, and may be a laser light source. The type of light source to be employed as the light source 21 may be appropriately selected according to detection conditions. The light source 21 may be combined with a light guiding optical system constituted by mirrors, lenses, and the like, to guide the excitation light beam toward an interface 12a between the dielectric prism substrate 22 and the metal film 12, as appropriate.

The dielectric prism substrate 22 may be formed by transparent materials such as transparent resins and glass. It is desirable for the dielectric prism substrate 22 to be formed by resin. In the case that the dielectric prism substrate 22 is formed by resin, polymethyl methacrylate (PMMA), polycarbonate (PC), and non crystalline polyolefin (APO) that includes cycloolefin may be favorably employed.

The material of the metal film 12 is not particularly limited, and may be selected appropriately according to detection conditions. However, it is desirable for Au, Ag, Pt, and the like to be employed, from the viewpoint of generation conditions for surface plasmon. The method for producing the metal film 12 is not particularly limited, and may be selected appropriately according to detection conditions and materials to be utilized. Examples of the method for producing the metal film 12 include: sputtering; vapor deposition; plating; a coating method that uses a metal colloid, and spraying. The film thickness of the metal film 12 is also not particularly limited, and may be selected appropriately according to detection conditions. However, it is desirable for the film thickness to be within a range from 20 nm to 60 nm, from the viewpoint of generation conditions for surface plasmon.

Examples of materials for the non flexible film 14 include silicon oxide and polymer materials. From the viewpoints of film forming conditions and surface processing conditions, it is desirable for polymer materials to be employed. In this case, a simple method, such as the spin coat method, may be employed to produce the non flexible film 14. The non flexible film 14 is formed by a hydrophobic material in the present invention. Therefore, molecules that cause light loss, such as metal ions and dissolved oxygen, which are present within the sample S, are prevented from entering the interior of the non flexible film 14. Accordingly, the excitation energy for the fluorescent labels F can be prevented from being robbed by these molecules.

As a specific material of the non flexible film 14, one that has a difference in the coefficient of linear (thermal) expansion compared to the material of the dielectric prism substrate 22 within a range of $35 \times 10^{-6}$ is desirable. Such a material may be selected from among those listed in Table 1.

TABLE 1

| Material | Coefficient of Linear (Thermal) Expansion ($\times 10^{-6}$) |
|---|---|
| Water | 70 |
| Polystyrene | 70 |
| PMMA | 70 |
| Polycarbonate | 60 |
| Cycloolefin (Zeonex ™ 330R) | 90 |
| Cycloolefin (Zeonex ™ E48R) | 60 |
| Quartz (SiO$_2$) | 0.6 |
| BK7 | 7.1 |
| Gold | 14 |

The reason why the difference in coefficients of linear (thermal) expansion is limited to within $35 \times 10^{-6}$ will be described below.

To improve stability with respect to environmental changes, and particularly temperature, it is preferable for the non flexible film 14 and the dielectric prism substrate 22 to have similar coefficients of thermal expansion. That is, if the coefficients of thermal expansion of the two components are different to a great degree, separation or decrease in the degree of close contact becomes likely when temperature changes occur. Specifically, it is desirable for the difference between the coefficients of linear (thermal) expansion of the two components to be within a range of $35 \times 10^{-6}$. Note that the metal film 12 is provided between the non flexible film 14 and the dielectric prism substrate 22. When temperature changes occur, the metal film 12 expands and contracts along with the non flexible film 14 above and the dielectric prism substrate 22 below. Therefore, the fact remains that it is preferable for the coefficients of thermal expansion of the non flexible film 14 and the dielectric prism substrate 22 to be similar. In consideration of the above points, in the case that the non flexible film 14 is formed by a polymer material, it is preferable to select resin as the material of the dielectric prism substrate 22 over glass.

Meanwhile, the film thickness of the non flexible film 14 is set to be within a range from 10 nm to 100 nm. The lower and upper limits of the film thickness are set to 10 nm and 100 nm for the following reasons.

Light loss occurs in molecules of fluorescent substances which are present in the vicinity of metal, due to energy transition to the metal. The degree of energy transition is inversely proportionate to the distance between the molecules and the metal to the third power in the case that the metal is a plane which is infinitely thick. The degree of energy transition is inversely proportionate to the distance between the molecules and the metal to the fourth power in the case that the metal is a plane which is infinitely thin. The degree of energy transition is inversely proportionate to the distance between the molecules and the metal to the sixth power in the case that the metal is in the form of fine particles. It is desirable for a distance of several nm or greater, preferably 10 nm or greater, to be secured between the metal film and the fluorescent substance molecules in the case that the metal is a metal film. Accordingly, the lower limit of the film thickness is set to 10 nm in the present invention. On the other hand, the fluorescent substance molecules are excited by near field light which leak from the surface of the metal film and which are amplified by surface plasmon. The range of travel (distance from the surface of the metal film) of near field light is at most approximately one wavelength, and it is known that the electric field intensity thereof attenuates drastically at an exponential rate corresponding to the distance from the surface of the metal film. When this relationship is calculated for visible light having a wavelength of 635 nm, it can be seen that leakage of the evanescent wave occurs only for a distance approximately corresponding to the wavelength (635 nm), and the electric field intensity drops drastically beyond 100 nm. It is desirable for the electric field that excites the fluorescent substance molecules to be as great as possible. Therefore, it is desirable to set the distance between the surface of the metal film and the fluorescent substance molecules to be 100 nm or less, to perform effective excitation. Accordingly, the upper limit of the film thickness is set to 100 nm in the present invention.

In the case that the non flexible film 14 is formed by a polymer, proteins and the like which are present as detection target substances 2 may be easily non specifically adsorbed onto the non flexible film. This is due to a hydrophobic effect caused by the polymer and the proteins being hydrophobic. In this case, the non specific adsorption of the proteins becomes a cause for deterioration in quantitative detection of fluorescence. Therefore, it is desirable for hydrophilic surface modifications to be provided on the surface of the non flexible film 14. The hydrophilic surface modifications may function as linkers to immobilize specific binding substances, in addition to the above function of preventing non specific adsorption.

The shape and the material of the sample holding section 13 is not particularly limited, as long as it is capable of holding the sample S such that the sample S is in contact with a detecting portion (more accurately, the non flexible film 21 in the first embodiment), and as long as it does not interfere with detection of the fluorescence emitted by the fluorescent labels F. In the case that the fluorescence is detected from above, the sample holding section 13 may be formed with side surfaces that do not transmit light and an upper surface that transmits light, as illustrated in FIG. 1, for example. Here, the side surfaces that do not transmit light are employed to shield light from the exterior from entering the sample holding section 13.

The photodetector 30 quantitatively detects fluorescence of a specific wavelength emitted by the fluorescent labels F. LAS-1000 plus by FUJIFILM Corporation may be employed as the photodetector 30. However, the photodetector 30 is not limited to the above, and may be selected appropriately according to detection conditions. Examples of alternative photodetectors include: CCD's; PD's (photodiodes); photoelectron multipliers; and c-MOS's.

The primary antibodies B1 are not particularly limited, and may be appropriately selected according to detection conditions. For example, in the case that the antigens A are CRP antigens (molecular weight: 110,000 Da), monoclonal antibodies (having at least different epitopes from the secondary antibodies B2) that specifically bind with the antigens A may be employed as the primary antibodies B1. The primary antibodies B1 may be immobilized onto the non flexible film 14, which is formed by a polymer material, by the amine coupling method via PEG's having carboxylized ends. Thereby, the antigens A can be immobilized on the non flexible film 21. The amine coupling method comprises the following three steps, for example. Note that the following example is for a case in which a 30 µl cuvette/cell is employed.

(1) Activation of —COOH Groups at the Ends of Linkers

30 µl of a solution containing equal volumes of a 0.1M NHS (N-hydrooxysuccinimide) solution and a 0.4M EDC (1-ethyl-3-(3-dimethylamminopropyl)carbodiimide) solution are added to the non flexible film 14, and left still at room temperature for 30 minutes.

(2) Immobilization of Primary Antibodies

Cleansing is performed five times with a PBS buffer (pH: 7.4). Then, 30 µl of a solution containing the primary antibodies (500 ug/ml) is added, and the non flexible film 14 is left still for 30 to 60 minutes at room temperature.

(3) Blocking of Non Reacted —COOH Groups

Cleansing is performed five times with a PBS buffer (pH: 7.4). Then, 30 µl of a 1M ethanol amine solution (pH: 8.5) is added, and the non flexible film 14 is left still for 20 minutes at room temperature. Thereafter, cleansing is performed five times with a PBS buffer (pH: 7.4).

Figure 2A:
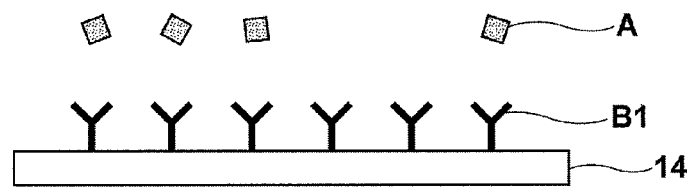
FIG. 2A, FIG. 2B, FIG. 2C, FIG. 2D, and FIG. 2E are schematic partial sectional diagrams that illustrate a fluorescence detecting process performed by a first embodiment of the present invention.
Figure 2B:
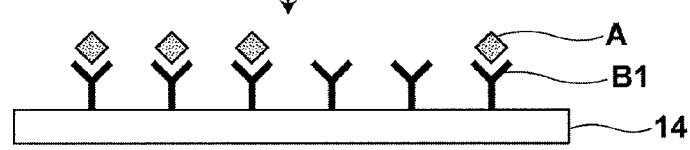
Figure 2C:
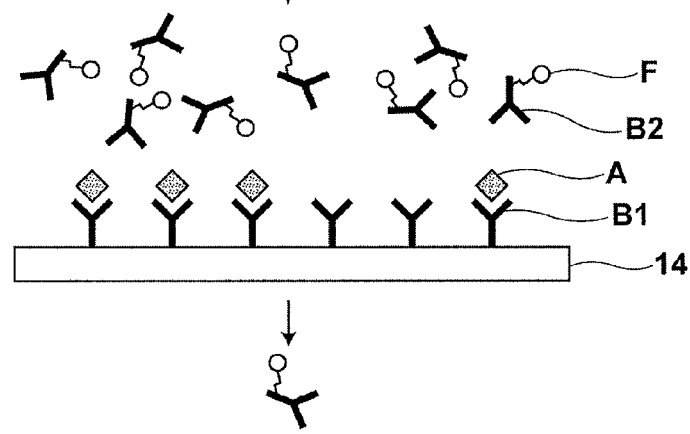
Figure 2D:
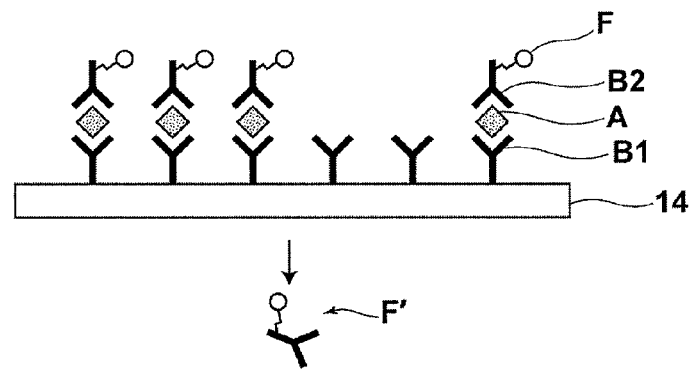
Figure 2E:
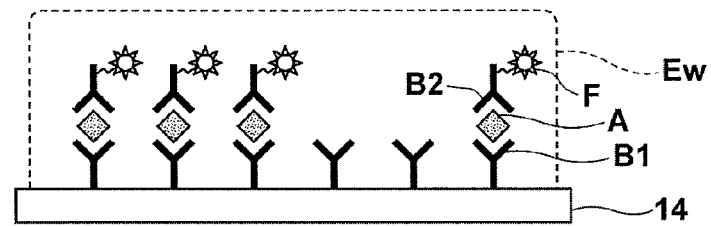

The fluorescence detecting method according to the first embodiment of the present invention includes the steps of: immobilizing the primary antibodies B1 onto the detecting portion that includes the metal film 12 formed on a surface of the dielectric prism substrate 22 via the hydrophilic surface modifications, and supplying the sample S containing the antigens A (FIG. 2A) to cause the antigens A to bind with the primary antibodies B1 (FIG. 2B); supplying the fluorescent labels F (FIG. 2C), causing the fluorescent labels F to bind to the antigens A, which are bonded to the primary antibodies B1, via the secondary antibodies B2 to immobilize the fluorescent labels F to the detecting portion by the sandwich method following step (FIG. 2D); causing the excitation light beam Li of a wavelength that causes the fluorescent labels F to emit light to enter the interface 12*a* between the dielectric prism substrate 22 and the metal film 12 through the dielectric prism substrate 22 such that conditions for total internal reflection are satisfied, to cause an electric field enhancing field Ew to be generated at the interface 12*a*; exciting the fluorescent labels F, which are immobilized on the detecting portion, with the electric field enhancing field Ew; and detecting the fluorescence emitted by the fluorescent labels F (FIG. 2E). As illustrated in FIG. 3, a plurality of fine metallic particles P are dispersed on the detecting portion when fluorescence is detected by the photodetector 30.

Here, the presence of the fluorescent labels F is actually confirmed by the detection of fluorescence. However, it is considered that the fluorescent labels F are bonded to the antigens A by the preliminary process. Therefore, the presence of the antigens A is indirectly confirmed by confirming the presence of the fluorescent labels F.

The fluorescent labels F are not particularly limited, as long as they emit fluorescence of a predetermined wavelength when excited by the excitation light beam Li. The fluorescent labels F may be selected appropriately according to measurement conditions. In the case that the wavelength of the excitation light beam La is approximately 650 nm, Cy5 pigment or the like may be employed. In this case, the fluorescent labels F can specifically bind to the antigens A, by modifying the fluorescent labels F with monoclonal antibodies (the secondary antibodies B2, having different epitopes from those of the primary antibodies B1) or the like. Note that the timing at which the fluorescent labels F and the secondary antibodies B2 are supplied is not particularly limited, and the fluorescent labels F may be added to the sample S in advance, prior to the detection target substance (the antigens A) binding to the primary antibodies B1.

The material of the fine metallic particles P is not particularly limited. However, Au, Ag, Cu, Pt, Ni, Ti, and the like are preferred, because they are superior in the ability to effectively induce localized plasmon, and superior in chemical stability (with respect to the sample S). In addition, the shapes of the fine metallic particles P are not particularly limited.

However, spherical shapes and rod like shapes are preferable, and rod like shapes (nano rods) are particularly preferable because they are capable of being densely dispersed on the detecting portion. It is preferable for the particle sizes of the fine metallic particles P to be smaller than the wavelength of the excitation light beam Li, and particles sizes within a range from 40 nm to 200 nm are particularly preferable. Here, the term "particle size" refers to the largest dimension of the fine particles. The timing at which the fine metallic particles P are dispersed on the detecting portion is not limited. However, it is preferable for the fine metallic particles P to be dispersed prior to the detection of fluorescence. In the case of the first embodiment, it is preferable for the fine metallic particles P to be dispersed on the detecting portion following the step in which the antigens A and the fluorescent labels F are immobilized onto the detecting portion. Further, it is preferable for the amount of fine metallic particles P to be dispersed on the detecting portion to be approximately $10^6/mm^2$, to balance dense dispersion and efficient readout of light.

In the first embodiment, each of the fine metallic particles P is covered by a dielectric layer 41, which is formed by a dielectric material. Thereby, the fluorescent labels F are prevented from approaching the fine metallic particles P to a distance at which metallic quenching occurs.

Two examples of methods for forming the dielectric layers 41 that cover the fine metallic particles P are listed below. Note that fine gold particles are employed as the fine metallic particles P in the methods described below.

The first method forms the dielectric layers 41 from an $SiO_2$ film, and includes the following three steps (1) through (3).
(1) Synthesis of gold colloids which are to become the fine gold particles.
(2) Substitution of surface scattering agent of the gold colloids (from citric acid to siloxane).

2.5 ml of a 1 mmol APS ((3-aminopropyl)trimethoxysilane) solution is added to 500 ml of a 5x=10-4 mol gold colloid solution, and agitated for 15 minutes, to substitute the citric acid on the surfaces of the gold colloids.
(3) Surface modification of the gold colloids with $SiO_2$ 20 ml of a 0.54 weight % sodium silicate solution, of which the pH has been adjusted to be within a range from 10 to 11, is added to the gold colloid solution of step (2), and agitated. After 24 hours, $SiO_2$ films having thicknesses of approximately 4 nm are formed. The solution is concentrated to 30 ml by centrifugal separation, and 170 ml of ethanol is added thereto. Further, 0.6 ml of $NH_4OH$ (28%) is dripped into the solution, 80 μl of TES (tetraoxysilane) is added, and mixed slowly for 24 hours, to form the dielectric layers 41 formed by $SiO_2$ films having thicknesses of 20 nm.

A case in which the dielectric layers 41 are formed by polymer films will be described as the second example of the method for forming the dielectric layers 41. This method includes the following two steps (1) and (2).
(1) Redispersion of Gold Nano Particles in DMF 1 ml of a water dispersed liquid containing at most 360 pmol (=$7 \times 10^{-11}$ weight %) of citric acid stabilized gold nano particles having an average particle size of 30 nm is prepared. The water dispersed liquid is subjected to centrifugal separation, then 0.95 ml of the supernatant liquid is discarded. The remaining dark red viscous sediment is redispersed in 1 ml of DMF (N, N-dimethylformamide). Note that excess citric acid ions hinder capsulation of particles. In addition, in the case that particles having small particle sizes are employed, it is better to cleanse the particles with water prior to adding DMF.
(2) Capsulation of Gold Nano Particles 1 ml of the DMF dispersion liquid that includes citric acid stabilized gold nano particles having an average particle size of approximately 30 nm (particle sizes may be measured by direct observation using a transmissive electron microscope, or by conversion from light absorbing spectra) at approximately 648 pmol (=$7 \times 10^{-11}$ weight %) is obtained in step (1) above. 10 μl of a DMF polystyrene-polyacrylic acid block copolymer solution (approximately 100-mer polystyrene and approximately 13-mer polyacrylic acid at $10^{-2}$ g/ml) is added, 200 μl of water is added at a flow rate of 8.3 μl/min by a syringe pump, and the mixture is agitated for 10 minutes. After 10 minutes of agitation, the color of the solution gradually changes to purple. At this time, 5 μl of a 1 weight % dodecanethiol DMF solution is added to the mixture, and agitated for 24 hours. Then, 3 ml of water is added at a flow rate of 2 ml/hour by a syringe pump.

Next, the DMF is removed over 24 hours by dialysis. Then, 72 μl of an EDC solution (0.1 weight % with respect to water: 24 nmol) is added at once while the mixture is being agitated, and after 30 minutes of agitation, 144 μl of an EDODEA solution (0.1 weight % with respect to water: 96 nmol) is added at once, and the mixture is continued to be agitated.

Thereafter, the reagents are removed by 24 hours of dialysis, and the remaining mixture is subjected to 30 minutes of centrifugal separation at 4000G's. Following the centrifugal separation, supernatant liquid corresponding to 80% of the total volume is discarded. Then, water of the same volume as the removed liquid is added to the mixture, and the centrifugal separation operation is performed again. By repeating the operation from centrifugal separation operation to centrifugal separation operation three times, dielectric layers 41 constituted by coating films of the polystyrene-polyacrylic acid block copolymers are formed around the gold nano particles (fine gold particles).

Hereinafter, the fluorescence detecting method according to the first embodiment, realized by the fluorescence detecting apparatus described above will be described.

The primary antibodies B1 that specifically bind with the antigens A are immobilized on the non flexible film 14. The sample S is caused to flow within the sample holding section 13, and the antigens A bind to the primary antibodies B1 and become immobilized onto the non flexible film 14. Next, the fluorescent labels F which have been treated to specifically bind to the antigens A are caused to flow within the sample holding section 13. The fluorescent labels F are immobilized on the detecting portion via the antigens A, which are bonded to the primary antibodies B1, and the secondary antibodies B2 (the sandwich method).

Then, the excitation light beam Li emitted by the light source 21 is caused to enter the interface 12a between the dielectric prism substrate 22 and the metal film 12 through the dielectric prism substrate 22 such that conditions for total internal reflection are satisfied. At this time, evanescent waves are generated at the interface 12a and surface plasmon is generated within the metal film 12 by resonance with the evanescent waves. Thereafter, the fluorescent labels F are excited by the evanescent waves (electric field enhancing field Ew), which is amplified by the electric field amplification effect of the surface plasmon. The excited fluorescent labels F emit fluorescence of a predetermined wavelength, and the antigens A can be detected by detecting the emitted fluorescence.

In the first embodiment, the fluorescence is detected by the photodetector 30 in a state in which the plurality of fine metallic particles P are dispersed on the detecting portion. Thereby, hot spots 40 which are generated in the gaps among the fine metal particles P or the gaps among the fine metal particles P and the metal film 12 can enhance the fluorescence generated by the fluorescent labels F which are present within the hot spots 40. The hot spots 40 are local regions at which static electric forces become concentrated (electric field concentration) at fine structures when the fine metallic particles P and the metal film 12 are at distances of approximately 10 nm from each other, and as a result, form locally strong electric fields.

Particularly at hot spots 40 which are formed in gaps among the fine metallic particles P or in gaps among the fine metallic particles P and the metal film 12, the electric field which is enhanced by the aforementioned plasmon is concentrated, to form great electric fields. At the same time, a synergistic effect that the great electric fields induce plasmon in the fine metallic particles P or in the metal film 12 even further is generated. Therefore, an electric field enhancing field having a far greater intensity will be generated compared to cases in which a single particle is present, or cases in which non metallic particles are in close proximity to each other. For example, in the case that two fine metallic particles P are several nm away from each other, the hot spot which is generated in the gap therebetween will be $10^6$ or greater, as described in Y. Inouye and S. Kawata, "Near field Raman spectroscopy and imaging using a tip enhanced field", Spectral Researches, Vol. 51, No. 6, pp. 276-285, 2002.

As a result, a fluorescence detecting method which is more simple and realized as a lower cost than Raman spectroscopy enables high sensitivity detection on the order of the molecular level.

Meanwhile, the plurality of fine metal particles P are widely dispersed on the detecting portion. Therefore, the hot spots 40 can be formed over a wide range. As a result, measurements can be performed within short periods of time over a wider range compared to Raman spectroscopy, in which a region that exhibits electric field enhancing effects is limited to the vicinity of the tip of a metallic probe.

In addition, fine metallic particles have greater scattering power with respect to light compared to other fine particles having similar volumes. Therefore, the scattered light can be employed as secondary excitation light, to more efficiently cause the fluorescent pigments to emit light.

Further, in the fluorescence detecting method according to the first embodiment, the non flexible film 14 is provided, to prevent energy transfer from the fluorescent labels F to the metal film 12 that causes metallic quenching. Therefore, the excited fluorescent labels F can be efficiently caused to emit light.

The dielectric layers 41 are formed to cover the fine metallic particles P, and therefore metallic quenching of fluorescence to the fine metallic particles P can also be prevented by the same principle as that described above.

The electric field enhancing field Ew only reaches regions within several hundred nanometers from the interface 12a. Therefore, it is possible to increase the amount of fluorescent labels F which are excited by the electric field enhancing field Ew, by concentrating the pairs of antigens A and fluorescent labels F at the detection portion by using the primary antibodies B1. Thereby, a greater intensity of fluorescence can be obtained, and as a result, highly quantitative fluorescence detection is enabled. Note that the extremely short propagation distance of the electric field enhancing field Ew is effective in improving S/N ratios, because the influence of light scattering due to impurities 90 in the samples and fluorescence emissions from floating fluorescent labels F' can be reduced.

Second Embodiment

FIG. 4 is a schematic sectional diagram that illustrates the vicinity of a detecting portion, on which fine metallic particles P are dispersed, in a fluorescence detecting apparatus that executes a fluorescence detecting method according to a second embodiment of the present invention. The fluorescence detecting apparatus which is utilized in the second embodiment is the same as that which is illustrated in FIG. 1 and was described as the first embodiment. Meanwhile, the fluorescence detecting method according to the second embodiment differs from the fluorescence detecting method according to the first embodiment in that the wavelength of the excitation light beam Li is a specific wavelength which is capable of inducing localized plasmon in the fine metallic particles P. For this reason, the elements of the fluorescence detecting apparatuses are the same, and detailed descriptions of the elements will be omitted insofar as they are not particularly necessary.

In the fluorescence detecting method of the second embodiment, the wavelength of the emitted excitation light beam Li is a specific wavelength which is capable of inducing localized plasmon in the fine metallic particles P, as described above. Therefore, localized plasmon is generated at the fine metallic particles P.

The wavelength of the excitation light beam Li is not particularly limited, and may be appropriately selected according to measurement conditions, such as the detection target substance and fluorescent labels, such that local plasmon is induced in the fine metallic particles P.

The fine metallic particles P are similar to those employed in the first embodiment. However, the particle sizes thereof are appropriately selected according to the wavelength of the excitation light beam Li such that local plasmon can be induced thereby.

Hereinafter, the fluorescence detecting method according to the second embodiment, realized by the fluorescence detecting apparatus described above will be described.

In the second embodiment as well, the plurality of fine metallic particles P are dispersed on the detecting section when a photodetector 30 detects fluorescence. Therefore, the same advantageous effects as those obtained by the first embodiment can be obtained.

Further, in the second embodiment, because the local plasmon is generated, near field light NL which is enhanced by the local plasmon leaks into the periphery of the fine metal particles P, as illustrated in FIG. 4. The near field light NL is generated independent of the aforementioned hot spots 40, and therefore do not influence the formation of the hot spots 40. That is, both formation of the hot spots 40 and generation of the near field light NL occur in the second embodiment. Accordingly, the fluorescent labels F can be excited not only by the hot spots 40 but by the near field light NL as well. As a result, fluorescence detection at an even higher sensitivity is enabled.

Third Embodiment

FIG. 5 is a schematic sectional diagram that illustrates the vicinity of a detecting portion, on which fine metallic particles P are dispersed, in a fluorescence detecting apparatus that executes a fluorescence detecting method according to a third embodiment of the present invention. The fluorescence detecting apparatus which is utilized in the third embodiment is the same as that which is illustrated in FIG. 1 and was described as the first embodiment. However, the fluorescence detecting method of the third embodiment differs from the fluorescence detecting method of the first embodiment, in that fluorescent labels which are used to label a detection target substance are constituted by an anti quenching fluorescent material, in which fluorescent pigment molecules are enveloped in an anti quenching material that transmits fluorescence generated by the fluorescent pigment molecules and prevents metallic quenching, and in that the dielectric layers 41 that cover the fine metallic particles P are not necessary. For this reason, the elements of the fluorescence detecting apparatuses are the same, and detailed descriptions of the elements will be omitted insofar as they are not particularly necessary.

In the fluorescence detecting method according to the third embodiment, fluorescent labels F which are used to label a detection target substance are constituted by an anti quenching fluorescent material FB, in which fluorescent pigment molecules 15 are enveloped in an anti quenching material 16 that transmits fluorescence generated by the fluorescent pigment molecules 15 and prevents metallic quenching, as described above.

It is preferable for the particle size of each anti quenching fluorescent material FB to be 5300 nm or smaller. It is further preferable for the particle size of each anti quenching fluorescent material FB to be 500 nm or smaller, and particle sizes within a range from 130 nm to 500 nm are particularly preferable. The preferred particle size was calculated in the following manner.

In fluorescence detection utilizing surface plasmon excitation, it is necessary to take disturbances of surface plasmon due to the anti quenching fluorescent material into consideration.

The material for the anti quenching fluorescent material has a higher refractive index than a water solvent. For example, the refractive index n of polystyrene is within a range from 1.59 to 1.6. The generation of surface plasmon is hindered by the anti quenching fluorescent material having such a high refractive index being positioned in the vicinity of the metal film. This phenomenon was considered for an approximated multilayer structure divided into a prism layer 101, a metal film 102, and a solvent layer 103. FIG. 6A is a diagram that schematically illustrates electric fields E which are generated on the surface of the metal film 102 by a light beam entering through the prism layer 101 in the case that only a water solvent layer is present. FIG. 6B is a diagram that schematically illustrates electric fields E which are generated on the surface of the metal film 102 by a light beam entering through the prism layer 101 in the case that a polystyrene anti quenching substance 104 is present on the metal film 102.

Figure 7:
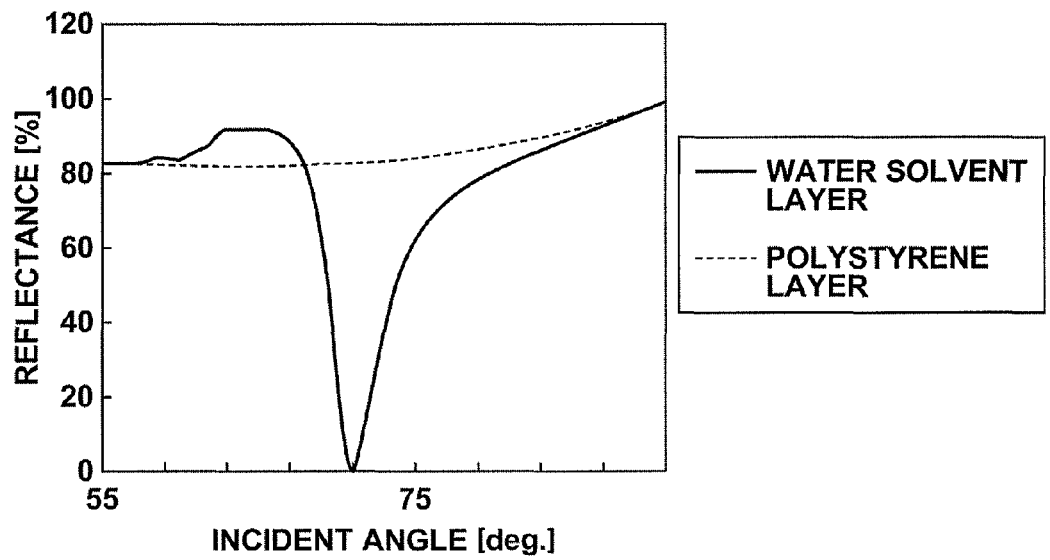
FIG. 7 is a graph that illustrates simulated relationships between the incident angle of an excitation light beam into an interface and reflectance in the cases illustrated in FIG. 6A and FIG. 6B.

It is assumed that the prism layers 101 and the solvent layer 103 (solvent layer 103') are of sufficient film thicknesses, and that the refractive index of the prism layer 101, the refractive index of the metal film 102, and the film thickness of the metal film 102 are already determined. In this case, the state of plasmon which is induced on the surface of the metal film 102 is determined by the refractive index of the solvent on the metal film 102. FIG. 7 is a graph that illustrates simulated relationships between the incident angle of an excitation light beam into an interface and reflectance in the case that only a water solvent is present on the metal film 102 (indicated by the solid line) and in the case that a polystyrene layer is present on the metal film 102 (indicated by the broken line). It can be understood from this graph that a resonance angle at which surface plasmon is generated exists in the case that the water solvent (refractive index=1.33) is present on the metal film 102, and that surface plasmon is not generated (a resonance angle does not exist) in the case that the polystyrene layer is present on the metal film 102. That is, the electric field is disturbed at the region of the broken line indicated by reference number 105, as illustrated in FIG. 6B. From this finding, it is assumed that surface plasmon is hindered and reduced, thereby precluding SPF measurement, if assays are performed using anti quenching fluorescent materials having high refractive indices (such as polystyrene and glass), and the anti quenching fluorescent materials are immobilized in the vicinity of the metal films.

Figure 8:
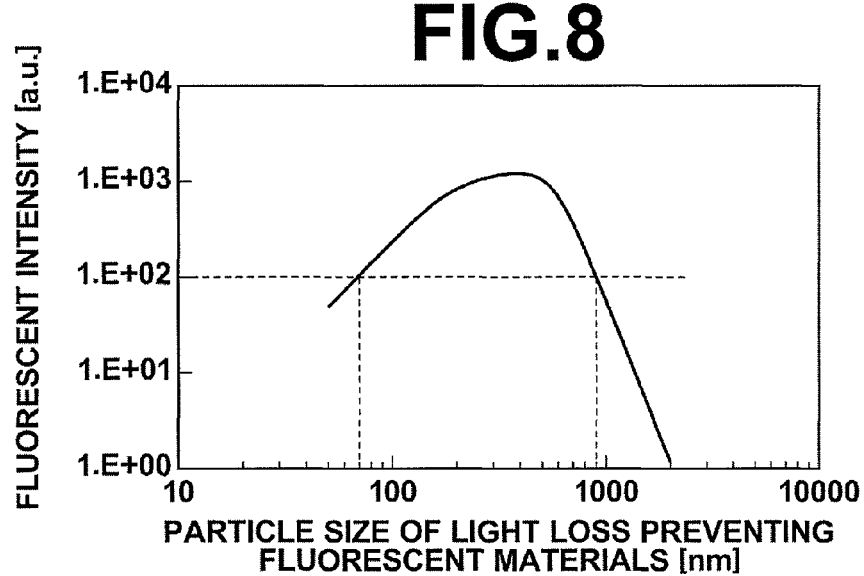
FIG. 8 is a graph that illustrates the relationship between particle sizes of anti quenching fluorescent materials and detected fluorescent intensities.

A simulated relationship that illustrates fluorescence intensities and the particle sizes of anti quenching fluorescent materials as a result of taking the disturbance of surface plasmon by anti quenching fluorescent materials into consideration is illustrated in FIG. 8. The greater the particle size of the anti quenching fluorescent material, the greater the number of fluorescent pigment molecules enveloped therein increases. Therefore, the fluorescent intensity increases along with increases in the particle size up to 400 nm. However, it was seen that the fluorescent intensity decreases drastically at particle sizes that exceed 500 nm. This is because the aforementioned disturbance of surface plasmon by the anti quenching fluorescent material becomes greater at particle sizes that exceed 500 nm. From the results illustrated in the graph of FIG. 8, it can be seen that it is desirable for the particle size of the anti quenching fluorescent material to be within a range from 70 nm to 900 nm, in order to limit decreases in fluorescent intensity to an order of 10 from the maximum peak thereof, which occurs at a particle size of 300 nm. Note that in the foregoing description, the preferred range of particle sizes was determined assuming that the anti quenching fluorescent material is spherical in shape. However, the anti quenching fluorescent material may be of shapes other than spheres. In the case that the anti quenching fluorescent material is not spherical, average values of the maximum dimensions and minimum dimensions of the particles may be designated as the particle sizes.

Further, the preferred range of particle sizes for the anti quenching fluorescent material was derived from the viewpoint of two dimensional filling density during fluorescence detection on a two dimensional plane, because the primary antibodies are immobilized on the detecting portion.

For diagnostic purposes, it is generally necessary for antigen concentrations of approximately 1 pM (pico Mol: $\times 10^{-12}$ mol/L) to be detectable. The preferred range of particle sizes for the anti quenching fluorescent material was derived with sensitivity properties that enable detection of antigens at concentrations of 1 pM or less, with a dynamic range of two orders of ten, that is, up to 100 pM as a goal.

Figure 9:
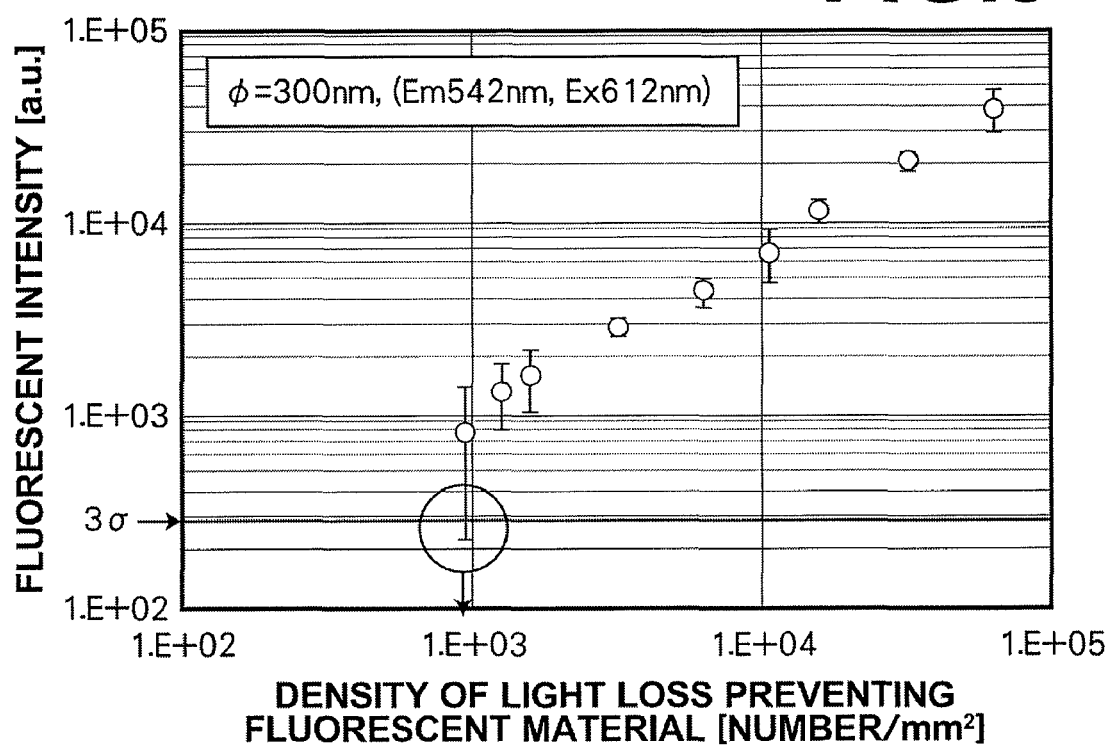
FIG. 9 is a graph that illustrates calibration curve data for the anti quenching fluorescent materials.

Regarding a specimen having an antigen concentration of 1 pM, assay conditions are assumed to be such that: the diameter of a detection region is 1 mm (area: 3.1 mm$^2$); the amount of the specimen to be caused to flow through a flow channel is 30 μl (this amount is a standard amount for specimens in common blood diagnostic devices, after blood cells are separated by a preliminary process or by a membrane filter); and the antigen capture rate is 0.2% (commonly, antigen capture rates are within a range from approximately 0.2% to approximately 2%; therefore, the antigen capture rate is assumed to be 0.2% such that detection is enabled with the minimum capture rate). In this case, it is necessary to immobilize and detect $1.2 \times 10^4$/mm antigens at the detection region. Here, $1.2 \times 10^4$/mm$^2$ is the target number of antigens to be immobilized. Calibration curve data for an incident light fluorescence detector (LAS-4000 by FUJIFILM) when anti quenching fluorescent materials (having diameters of 300 nm, an excitation wavelength of 542 nm, and a fluorescent wavelength of 612 nm) produced by the aforementioned steps were measured are illustrated in the graph of FIG. 9. The results illustrated here were obtained by employing excitation light having a central wavelength of 520 nm emitted by a green LED, and fluorescence was detected through a green fluorescent filter. The detection limit density at this time was $1.0 \times 10^3$/ mm², at which the error bar intersected the background value 3 σ (σ is a standard deviation) of the fluorescent detecting device.

From these results, it became clear that although 1/12 of the target number of immobilized antigens ($1.2\times10^4$/mm²), antigens can be detected at antigen concentrations of 1 pM or less, when anti quenching fluorescent materials having diameters of 300 nm are employed. In addition, it is also clear from these results that detection of antigens in specimens containing antigens at 1 pM is also possible even if the particle sizes of the anti quenching fluorescent materials are set to be less than 300 nm. In the case that the fluorescent pigment molecules are enveloped at the same density, the fluorescent intensity emitted by each anti quenching fluorescent material is proportionate to the cubed radius of the anti quenching fluorescent material. Accordingly, in the case that anti quenching fluorescent materials having diameters of 130 nm are employed, the fluorescent intensity emitted thereby becomes 1/12 that of the fluorescent intensity emitted by anti quenching fluorescent materials having diameters of 300 nm. However, this fluorescent intensity is sufficient to detect antigens at an antigen concentration of 1 pM. From these findings, the lower limit of the particle size of the anti quenching fluorescent materials that enable detection of antigens at an antigen concentration of 1 pM is determined to be approximately 130 nm. Note that here, it is assumed that the density of the fluorescent pigment molecules enveloped within the anti quenching fluorescent materials are substantially uniform.

The greater the particle size of the anti quenching fluorescent material, the greater the number of fluorescent pigment molecules enveloped therein becomes. Therefore, the detected fluorescent signal intensities increase along with increases in the particle size, which is advantageous from the viewpoint of detected fluorescent intensities. However, the number of anti quenching fluorescent materials which can be immobilized onto a predetermined area of a two dimensional surface is limited from the viewpoint of three dimensional interference. If the dynamic range is set to two orders of ten, that is, the upper limit of detectable concentrations is set to 100 pM, the number of anti quenching fluorescent materials that can be immobilized becomes $1.2\times10^4$/mm². At this time, the particle size at which maximum filling density is achieved, assuming that a single anti quenching fluorescent material binds with each antigen, is 500 nm. For this reason, the upper limit of the particle size for the anti quenching fluorescent materials is 500 nm.

The most preferred range of particle sizes for the anti quenching fluorescent materials is from 130 nm to 500 nm for the reasons described above.

Specific examples of the anti quenching material 16 include polystyrene and $SiO_2$. However, the material of the anti quenching material 16 is not particularly limited, as long as it is capable of enveloping the fluorescent pigment molecules 15 and transmitting the fluorescence emitted by the fluorescent pigments 15. The anti quenching fluorescent materials FB are the fluorescent pigment molecules 15 enveloped in the anti quenching materials 16. Therefore, it is not necessary for a film to be provided on the metal film 12 in order to prevent metallic quenching, because the fluorescent pigment molecules 15 and the metal film 12 are separated by sufficient distances by the anti quenching materials 16. Accordingly, metallic quenching can be prevented by an extremely simple method, while stably detecting fluorescent signals. A single fluorescent pigment molecule 15 may be enveloped in the anti quenching material 16 of each anti quenching fluorescent material FB. However, it is more preferable for a plurality of fluorescent pigment molecules 15 to be enveloped in the anti quenching material 16 of each anti quenching fluorescent material FB.

Note that specific examples of favorable combinations of light sources 21 and the anti quenching fluorescent materials FB are listed below.

A laser diode light source having a wavelength of 655 nm (DL-3147-160F or DL-3357-165 by StockerYale, Inc.) and an anti quenching fluorescent material (FC03F/8196 having a diameter of 510 nm, an excitation wavelength of 660 nm, and a fluorescent wavelength of 690 nm, by Bangs Laboratories, Inc.) or an anti quenching fluorescent material (F8807 having a diameter of 200 nm, an excitation wavelength of 660 nm, and a fluorescent wavelength of 680 nm, by Molecular Probes, Inc.)

A laser diode light source having a wavelength of 635 nm (DL-3148-023 or DL-3038-011 by StockerYale, Inc.) and an anti quenching fluorescent material (F8816 having a diameter of 1000 nm, an excitation wavelength of 625 nm, and a fluorescent wavelength of 645 nm, by Molecular Probes, Inc.)

An example of a method for modifying the anti quenching fluorescent materials FB with secondary antibodies B2, and a method for producing a labeling solution will be described.

A 50 mM MES buffer and a 5.0 mg/mL anti hCG monoclonal antibody solution (Anti hCG 5008 SP-5, by Medix Biochemica) are added to an anti quenching fluorescent material solution (FC03F/8196 having a diameter of 510 nm, an excitation wavelength of 660 nm, and a fluorescent wavelength of 690 nm, by Bangs Laboratories, Inc.) and agitated. Thereby, anti quenching fluorescent materials FB are modified with the antibodies.

Next, a 400 mg/mLESC solution (01-62-0011 by Wako Pure Chemical Industries, Ltd.) is added, and the mixture is agitated at room temperature.

Further, a 2 mol/L glycine solution is added and the mixture is agitated. Thereafter, the mixture is subjected to centrifugal separation, to cause the particles to settle.

Finally, supernatant liquid is removed, PBS (having a pH of 7.4) is added, and the anti quenching fluorescent materials are redispersed by an ultrasonic cleansing machine. Centrifugal separation is performed again, supernatant liquid is removed, 500 μL of a 1% BSA PBS solution (having a pH of 7.4) is added, and the anti quenching fluorescent materials are redispersed, to obtain the labeling solution.

Hereinafter, the fluorescence detecting method according to the third embodiment, realized by the fluorescence detecting apparatus described above will be described.

In the third embodiment as well, the plurality of fine metallic particles P are dispersed on the detecting section when a photodetector 30 detects fluorescence. Therefore, the same advantageous effects as those obtained by the first embodiment can be obtained.

Further, the anti quenching materials FB are employed as the fluorescent labels as in the third embodiment. Therefore, the fine metallic particles P and the fluorescent pigment molecules can be separated to a degree without providing films for preventing metallic quenching around the fine metallic particles P. The step of forming the dielectric layers 41, which were necessary to prevent metallic quenching due to the fine metallic particles P in the first and second embodiments, is obviated. Accordingly, metallic quenching can be prevented by an extremely simple method, while stably detecting fluorescent signals.

In addition, many fluorescent pigment molecules label each antigen A in the third embodiment. Meanwhile, fluorescent pigment molecules 15 which are at distances from the metal film at which sufficient excitation by the electric field enhancing fields Ew is not possible can be excited by scattered light Ls, which is the electric field enhancing fields Ew scattered by the fine metallic particles P. For these reasons, a greater number of fluorescent pigment molecules 15 can be excited in the third embodiment, in addition to the advantageous effects imparted by the hot spots 40 as in the first embodiment. Accordingly, fluorescence detection is enabled with even higher sensitivity.

<Design Modifications>

The above embodiments were described as cases in which the fine metallic particles P are dispersed in the solvent of the sample S, then fluorescence is detected. However, the present invention is not limited to such a configuration. Alternatively, fluorescence may be detected after the solvent is dried.

The method for drying the solvent is not particularly limited. Examples of drying method include static drying, and reduced pressure drying.

In this case, the fine metallic particles P can be agglomerated on the surface of the detecting portion. Therefore, the gaps among the fine metallic particles and the gaps among the fine metallic particles and the metal film can be made more dense, thereby improving the degree at which fluorescence is enhanced. In addition, the refractive index of the surrounding medium will decrease from that of water (1.33) to that of air (1.0). Thereby, there is an advantage that the electric field enhancing effect of plasmon and the hot spots is intensified.

What is claimed is:

1. A fluorescence detecting method, comprising the steps of:
    supplying a sample that includes a detection target substance labeled with fluorescent labels to a detecting portion that includes a metal film formed on a surface of a dielectric prism;
    causing an excitation light beam of a wavelength that causes the fluorescent labels to emit light to enter the interface between the dielectric prism and the metal film through the dielectric prism such that an electric field enhancing field is generated on the surface of the metal film; and
    detecting fluorescence emitted by fluorescent labels, which are attached to the detection target substance, generated due to an excitation effect of the electric field enhancing field, with a photodetector to detect the amount of the detection target substance which is present in the sample, based on the amount of detected fluorescence;
    the detection of the fluorescence being performed with a plurality of fine metallic particles dispersed on the detecting portion.

2. A fluorescence detecting method as defined in claim 1, wherein:
    the particle size of the fine metallic particles is within a range from 40 nm to 200 nm.

3. A fluorescence detecting method as defined in claim 2, wherein:
    the fine metallic particles are nano rods.

4. A fluorescence detecting method as defined in claim 3, wherein:
    the fluorescent labels are constituted by an anti quenching fluorescent material, in which fluorescent pigment molecules are enveloped in an anti quenching material that transmits fluorescence generated by the fluorescent pigment molecules and prevents metallic quenching.

5. A fluorescence detecting method as defined in claim 4, wherein:
    the fluorescence is detected by the photodetector after a solvent in the sample is dried.

6. A fluorescence detecting method as defined in claim 2, wherein:
    the fluorescent labels are constituted by an anti quenching fluorescent material, in which fluorescent pigment molecules are enveloped in an anti quenching material that transmits fluorescence generated by the fluorescent pigment molecules and prevents metallic quenching.

7. A fluorescence detecting method as defined in claim 6, wherein:
    the fluorescence is detected by the photodetector after a solvent in the sample is dried.

8. A fluorescence detecting method as defined in claim 1, wherein:
    the fine metallic particles are nano rods.

9. A fluorescence detecting method as defined in claim 8, wherein:
    the fluorescent labels are constituted by an anti quenching fluorescent material, in which fluorescent pigment molecules are enveloped in an anti quenching material that transmits fluorescence generated by the fluorescent pigment molecules and prevents metallic quenching.

10. A fluorescence detecting method as defined in claim 9, wherein:
    the fluorescence is detected by the photodetector after a solvent in the sample is dried.

11. A fluorescence detecting method as defined in claim 1, wherein:
    the fluorescent labels are constituted by an anti quenching fluorescent material, in which fluorescent pigment molecules are enveloped in an anti quenching material that transmits fluorescence generated by the fluorescent pigment molecules and prevents metallic quenching.

12. A fluorescence detecting method as defined in claim 11, wherein:
    the fluorescence is detected by the photodetector after a solvent in the sample is dried.

13. A fluorescence detecting method as defined in claim 1, wherein:
    a non flexible film of a hydrophobic material is formed at a film thickness within a range of 10 to 100 nm on the surface of the metal film opposite the dielectric prism.

14. A fluorescence detecting method as defined in claim 13, wherein:
    the non flexible film is constituted by a polymer material.

* * * * *